(12) United States Patent
Roeder et al.

(10) Patent No.: US 8,518,098 B2
(45) Date of Patent: Aug. 27, 2013

(54) SPLIT SHEATH DEPLOYMENT SYSTEM

(75) Inventors: Blayne A. Roeder, Lafayette, IN (US); Alan R. Leewood, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 888 days.

(21) Appl. No.: 11/707,448

(22) Filed: Feb. 16, 2007

(65) Prior Publication Data

US 2007/0233222 A1 Oct. 4, 2007

Related U.S. Application Data

(60) Provisional application No. 60/775,187, filed on Feb. 21, 2006.

(51) Int. Cl.
*A61F 2/44* (2006.01)

(52) U.S. Cl.
USPC .......................................... 623/1.11; 606/108

(58) Field of Classification Search
USPC ............................. 623/1.11, 17.13; 606/108
See application file for complete search history.

(56) References Cited

U.S. PATENT DOCUMENTS

| | | | |
|---|---|---|---|
| 4,562,596 A | 1/1986 | Kornberg | |
| 4,665,918 A | 5/1987 | Garza et al. | |
| 4,921,484 A | 5/1990 | Hillstead | |
| 4,950,227 A | 8/1990 | Savin et al. | |
| 5,078,720 A | 1/1992 | Burton et al. | |
| 5,092,877 A | 3/1992 | Pinchuk | |
| 5,192,297 A | 3/1993 | Hull | |
| 5,201,757 A * | 4/1993 | Heyn et al. ................. 606/198 |
| 5,366,504 A | 11/1994 | Andersen et al. | |
| 5,380,304 A | 1/1995 | Parker | |
| 5,405,377 A | 4/1995 | Cragg | |
| 5,415,664 A * | 5/1995 | Pinchuk ....................... 623/1.11 |
| 5,445,646 A | 8/1995 | Euteneuer et al. | |
| 5,456,713 A | 10/1995 | Chuter | |
| 5,464,449 A | 11/1995 | Ryan et al. | |
| 5,534,007 A | 7/1996 | St. Germain et al. | |
| 5,626,603 A | 5/1997 | Venturelli et al. | |
| 5,645,559 A | 7/1997 | Hachtman et al. | |

(Continued)

FOREIGN PATENT DOCUMENTS

| | | |
|---|---|---|
| EP | 0696447 B1 | 2/1996 |
| GB | 1205743 | 9/1970 |

(Continued)

OTHER PUBLICATIONS

Memotherm Billiary Stents, Product brochure, Angiomed, 6 pages, Nov. 1993.

(Continued)

*Primary Examiner* — S. Thomas Hughes
*Assistant Examiner* — Julie A Szpira
(74) *Attorney, Agent, or Firm* — Brinks Hofer Gilson & Lione

(57) ABSTRACT

A device for delivering and deploying a radially expandable prosthesis is disclosed and comprises a proximal prosthesis release mechanism having a first resistance and a distal prosthesis release mechanism having a second resistance. The device further comprises an actuation mechanism for actuating the distal and proximal release mechanisms in a single coordinated movement and a biasing compensator for regulating the relationship between the first resistance and the second resistance. Additional aspects of the invention include devices and methods for delivering and deploying a radially expandable prosthesis.

21 Claims, 4 Drawing Sheets

(56) References Cited

U.S. PATENT DOCUMENTS

| | | |
|---|---|---|
| 5,683,451 A | 11/1997 | Lenker et al. |
| 5,690,644 A | 11/1997 | Yurek et al. |
| 5,693,086 A | 12/1997 | Goicoechea et al. |
| 5,707,376 A | 1/1998 | Kavteladze et al. |
| 5,817,101 A | 10/1998 | Fiedler |
| 5,817,102 A | 10/1998 | Johnson et al. |
| 5,824,041 A | 10/1998 | Lenker et al. |
| 5,876,448 A | 3/1999 | Thompson et al. |
| 5,906,619 A | 5/1999 | Olson et al. |
| 6,004,328 A | 12/1999 | Solar |
| 6,024,763 A | 2/2000 | Lenker et al. |
| 6,056,759 A | 5/2000 | Fiedler |
| 6,113,608 A * | 9/2000 | Monroe et al. ............... 623/1.11 |
| 6,123,723 A | 9/2000 | Konya et al. |
| 6,203,550 B1 | 3/2001 | Olson |
| 6,206,888 B1 | 3/2001 | Bicek et al. |
| 6,254,611 B1 | 7/2001 | Vrba |
| 6,287,315 B1 | 9/2001 | Wijeratne et al. |
| 6,305,436 B1 | 10/2001 | Andersen et al. |
| 6,336,938 B1 | 1/2002 | Kavteladze et al. |
| 6,350,278 B1 | 2/2002 | Lenker et al. |
| 6,402,760 B1 | 6/2002 | Fedida |
| 6,514,261 B1 | 2/2003 | Randall et al. |
| 6,579,297 B2 | 6/2003 | Bicek et al. |
| 6,605,109 B2 | 8/2003 | Fiedler |
| 6,626,934 B2 | 9/2003 | Blaeser et al. |
| 6,652,480 B1 | 11/2003 | Imran et al. |
| 6,669,716 B1 | 12/2003 | Gilson et al. |
| 6,849,084 B2 | 2/2005 | Rabkin et al. |
| 6,858,034 B1 | 2/2005 | Hijlkema et al. |
| 6,911,039 B2 | 6/2005 | Shiu et al. |
| 7,105,016 B2 | 9/2006 | Shiu et al. |
| 7,122,050 B2 | 10/2006 | Randall et al. |
| 7,419,501 B2 | 9/2008 | Chiu et al. |
| 2001/0012944 A1 * | 8/2001 | Bicek et al. ............... 606/108 |
| 2001/0034514 A1 | 10/2001 | Parker |
| 2002/0045929 A1 | 4/2002 | Diaz |
| 2003/0109886 A1 | 6/2003 | Keegan et al. |
| 2003/0220682 A1 | 11/2003 | Kujawski |
| 2004/0093063 A1 | 5/2004 | Wright et al. |
| 2004/0098079 A1 | 5/2004 | Hartley et al. |
| 2004/0106974 A1 | 6/2004 | Greenberg et al. |
| 2004/0127912 A1 | 7/2004 | Rabkin et al. |
| 2004/0133264 A1 | 7/2004 | Moore |
| 2004/0148008 A1 | 7/2004 | Goodson, IV et al. |
| 2005/0060018 A1 | 3/2005 | Dittman |
| 2005/0080476 A1 | 4/2005 | Gunderson et al. |
| 2005/0085890 A1 | 4/2005 | Rasmussen et al. |
| 2005/0090887 A1 | 4/2005 | Pryor |
| 2005/0273151 A1 | 12/2005 | Fulkerson et al. |
| 2006/0286145 A1 | 12/2006 | Horan et al. |
| 2007/0060999 A1 | 3/2007 | Randall et al. |
| 2007/0255390 A1 | 11/2007 | Ducke et al. |
| 2008/0021538 A1 | 1/2008 | Wright et al. |

FOREIGN PATENT DOCUMENTS

| | | |
|---|---|---|
| WO | WO 94/03127 A1 | 2/1994 |
| WO | WO 95/11055 A1 | 4/1995 |
| WO | WO 98/53761 A1 | 12/1998 |
| WO | WO 2007/084370 A1 | 7/2007 |

OTHER PUBLICATIONS

Memotherm Tips Stents, Product brochure, Angiomed, 6 pages, Nov. 1993.

* cited by examiner

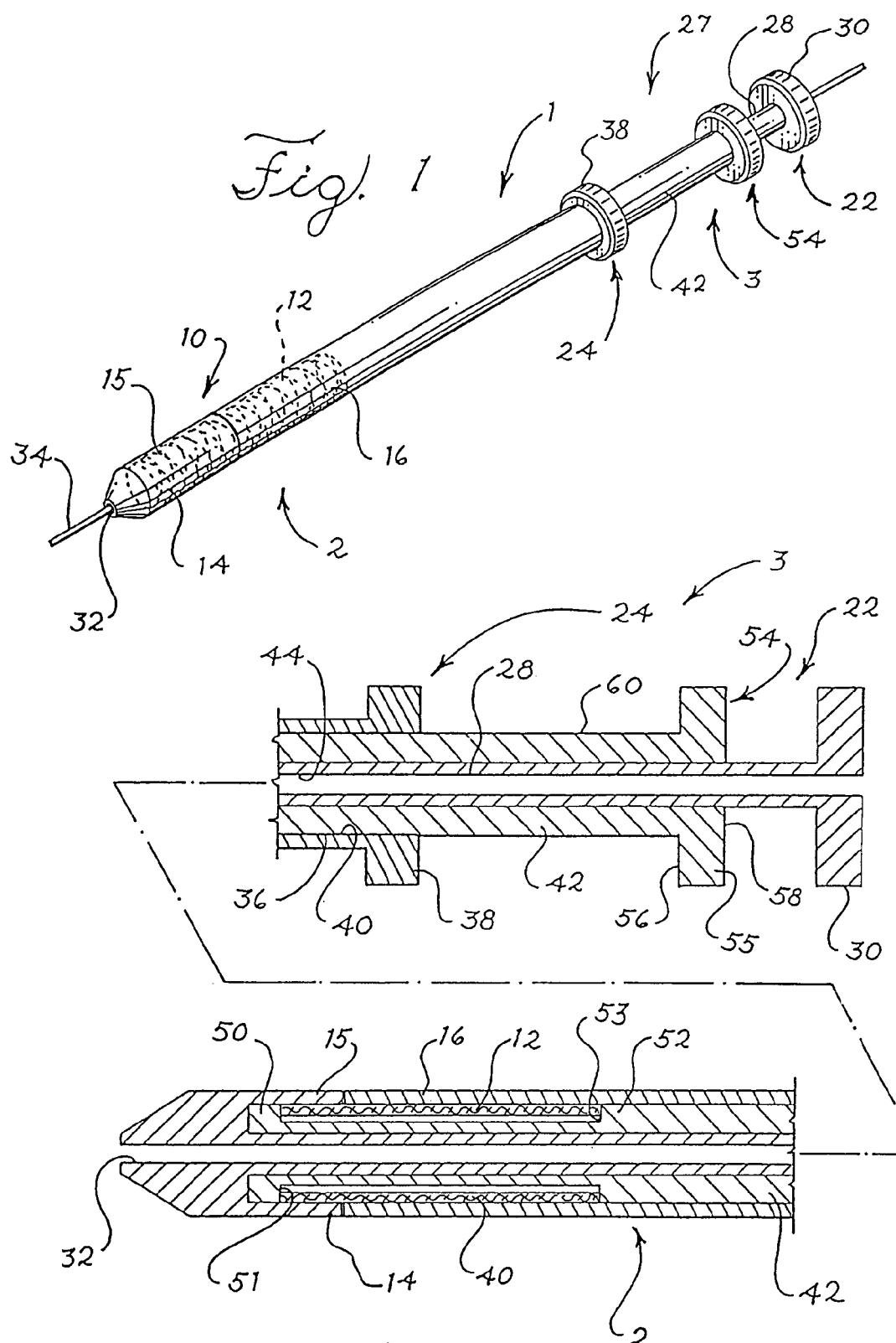

SPLIT SHEATH DEPLOYMENT SYSTEM

RELATED APPLICATIONS

This application claims the benefit of the filing date under 35 U.S.C. §119(e) of U.S. Provisional Patent Application Ser. No. 60/775,187, filed Feb. 21, 2006, which is incorporated herein by reference.

BACKGROUND OF THE INVENTION

1. Field of the Invention

This invention relates to medical devices and, in particular, to delivery and deployment devices for self-expanding prostheses and methods of delivering and deploying a prosthesis into a body lumen.

2. Description of Related Art

Expandable prostheses, such as stents and stent grafts, are used for treating damaged or diseased body lumens such as the esophagus, bile duct, and blood vessels. The deployment of intraluminal prostheses into the lumen of a patient from a remote location by the use of a delivery and deployment device is well known in the art. Generally, an expandable intraluminal prosthesis is placed on a delivery and deployment device in a radially reduced state and inserted percutaneously into a body lumen. Once the prosthesis is properly positioned, the prosthesis may be radially expanded using means well known in the art. For example, the prosthesis may be expanded using a balloon catheter device.

Alternatively, the prosthesis may be radially self-expanding. Where the prosthesis is radially self-expanding, the delivery and deployment device will include means for retaining the prosthesis in a radially constrained state. For example, U.S. Pat. No. 4,562,596 entitled "Aortic Graft, Device and Method for Performing an Intraluminal Abdominal Aortic Aneurysm Repair," which is herein incorporated by reference, proposes retaining a self-expanding graft within a sleeve until it is to be deployed, at which time the sleeve is withdrawn and the graft is allowed to expand. U.S. Pat. No. 4,665,918 entitled "Prosthesis System and Method," which is herein incorporated by reference, proposes a system and method for the deployment of a prosthesis in a blood vessel. The prosthesis is positioned between a delivery catheter and an outer sheath, and expands outwardly upon removal of the sheath.

A problem with conventional delivery and deployment systems for radially self-expanding prostheses is that the accuracy and precision of prosthesis placement is dependent on the axial stiffness of the prosthesis. During deployment, the delivery and deployment device imposes stresses on the prosthesis, for example, via friction between the retaining sleeve and the prosthesis. Axially stiff prostheses are generally capable of absorbing these stresses without exhibiting significant axial shortening or elongation. Axially flexible stents, however, are more sensitive to axial stresses and may be more prone to exhibit axial shortening or elongation during deployment, resulting in potentially inaccurate or imprecise prosthesis placement in the body lumen. There is a growing need for axially flexible prostheses that are capable of conforming with highly deformable luminal environments, such as the superficial femoral artery. Accordingly, there is a need in the art for a prosthesis deployment system that reduces or eliminates the problem of axial shortening or elongation.

U.S. Pat. No. 5,201,757 entitled "Medial Region Deployment of Radially Self-Expanding Stents," which is herein incorporated by reference, proposes an apparatus for deploying a radially self-expanding stent. The apparatus includes proximal and distal sleeves for containing proximal and distal end portions of the stent in a reduced radius delivery configuration. The sleeves are moved axially relative to one another to permit radial self-expansion of the stent. A problem with this system is that it does not provide the operator with sufficient control over the manner of deployment. For example, if the operator wishes to deploy the prosthesis in a single quick motion, he will be unable to control the rate or the order of deployment of the proximal and distal prosthesis ends. This is because the manner of deployment can be significantly impacted by internal frictional stresses that can vary from device to device. The operator may also wish to deploy the distal sleeve prior to the proximal sleeve, or the proximal sleeve prior to the distal sleeve. Alternatively, the operator may wish to deploy the proximal and distal sleeves concurrently. The system disclosed in U.S. Pat. No. 5,201,757, however, is generally not capable of providing this level of control to the operator. As a consequence, there is a need in the art for a prosthesis deployment system that solves these and other problems.

SUMMARY

According to an aspect of the invention, a device for delivering and deploying a radially expandable prosthesis is provided and comprises a proximal release mechanism for selectively releasing a proximal portion of the prosthesis, a distal release mechanism for selectively releasing a distal portion of the prosthesis, and an actuation mechanism for actuating the proximal and distal release mechanisms in a single coordinated movement.

The proximal release mechanism comprises a proximal sheath that is radially disposed over a proximal portion of a prosthesis. The proximal sheath is slidable proximally relative to the prosthesis to release the proximal portion of the prosthesis. The distal release mechanism comprises a distal sheath that is radially disposed over a distal portion of the prosthesis. The distal sheath is slidable distally relative to the prosthesis to release the distal portion of the prosthesis. The proximal release mechanism has a first resistance and the distal release mechanism has a second resistance.

The relationship between the first and second resistances affects the manner of deployment of the distal sheath and the proximal sheath when the actuation mechanism is deployed in a single coordinated movement. According to an aspect of the invention, the delivery and deployment device may comprise a biasing compensator for regulating the relationship between the first resistance and the second resistance. By regulating the relationship between the first and second resistances, the biasing compensator may control the displacement of the proximal sheath relative to the distal sheath when the actuation mechanism is deployed. At least one or both of the proximal and distal release mechanisms may comprise the biasing compensator. The device may comprise a plurality of biasing elements, where each of the distal and proximal release mechanisms includes at least one of the plurality of biasing elements.

The biasing compensator may comprise one or more springs, for example, tension springs and/or compression springs. Alternatively, a biasing compensator may comprise other biasing elements, for example a bellows or a compressible gasket. Each of the proximal and distal release mechanisms may comprise the biasing compensator for regulating the displacement of the proximal sheath relative to the distal sheath.

According to another aspect of the invention, a device for delivering and deploying a radially expandable prosthesis is provided and comprises a first elongate member, a second elongate member, and a third elongate member. The first elongate member comprises a lumen and has a radially expandable prosthesis disposed over a distal portion thereof. The second elongate member is slidably disposed within the lumen of the first elongate member and comprises a distal sheath for releasably retaining a distal portion of the prosthesis. The third elongate member comprises a lumen and is slidably disposed over the first elongate member. The third elongate member comprises a proximal sheath for releasably retaining a proximal portion of the prosthesis. The delivery and deployment device may further comprise an actuation mechanism for moving the second elongate member distally relative to the first elongate member and the third elongate member proximally relative to the first elongate member to release the distal and the proximal portions of the prosthesis in a single coordinated movement.

The delivery and deployment device has a distal release resistance and a proximal release resistance. According to an aspect of the invention, the delivery and deployment device may comprise a biasing compensator for regulating the relationship between the distal release resistance and the proximal release resistance. The biasing compensator may comprise one or more biasing elements, as described throughout the specification and above, for example a spring, a compressible gasket, or a bellows. The biasing compensator may be connected to at least one of the second and third elongate members. Further, the delivery and deployment device may comprise a plurality of biasing elements, where one or more of the biasing elements are connected to each of the second and third elongate members.

According to another aspect of the invention, a limiting member may be provided for a delivery and deployment device that limits the displacement of the proximal sheath and/or the distal sheath during deployment.

According to another aspect of the invention, a method of delivering and deploying a radially expandable prosthesis into a body lumen is disclosed. The method comprises the step of providing a delivery and deployment device comprising a radially expandable prosthesis having a proximal end and a distal end, a proximal release mechanism for releasably retaining a proximal portion of the prosthesis, a distal release mechanism for releasably retaining a distal portion of the prosthesis, and an actuation mechanism for actuating the proximal and distal release mechanisms in a single coordinated movement. The method may further comprise the steps of providing a biasing compensator for regulating the deployment of the proximal release mechanism with respect to the distal release mechanism, positioning the delivery and deployment device in a body lumen so that the prosthesis is adjacent an area to be treated, and actuating the actuation mechanism so that the proximal release mechanism releases the proximal portion of the prosthesis and the distal release mechanism releases the distal portion of the prosthesis in a predetermined manner.

The delivery and deployment device may be configured in accordance with any of the teachings in the specification. For example, the proximal release mechanism may comprise a proximal sheath radially disposed over a proximal portion of the prosthesis and may be slidable proximally relative to the prosthesis to release the proximal portion of the prosthesis. Similarly, the distal release mechanism may comprise a distal sheath radially disposed over a distal portion of the prosthesis and may be slidable distally relative to the prosthesis to release the distal portion of the prosthesis.

The biasing compensator may comprise any of the biasing elements described throughout the specification, including, but not limited to, a spring, a bellows, or a compressible gasket. According to an aspect of the invention, the actuating step may comprise actuating the proximal release mechanism prior to the distal release mechanism, the distal release mechanism prior to the proximal release mechanism, or the proximal and distal release mechanisms generally concurrently. Alternatively, or additionally, the actuating step may comprise releasing the proximal end of the prosthesis prior to the distal end, the distal end prior to the proximal end, or releasing the proximal and distal ends of the prosthesis generally concurrently.

BRIEF DESCRIPTION OF THE DRAWINGS

FIG. 1 is a perspective view of a delivery and deployment device according to an aspect of the present invention;

FIG. 2 is a cross-sectional view of the device of FIG. 1;

DETAILED DESCRIPTION OF THE PREFERRED EMBODIMENTS

Figure 3:
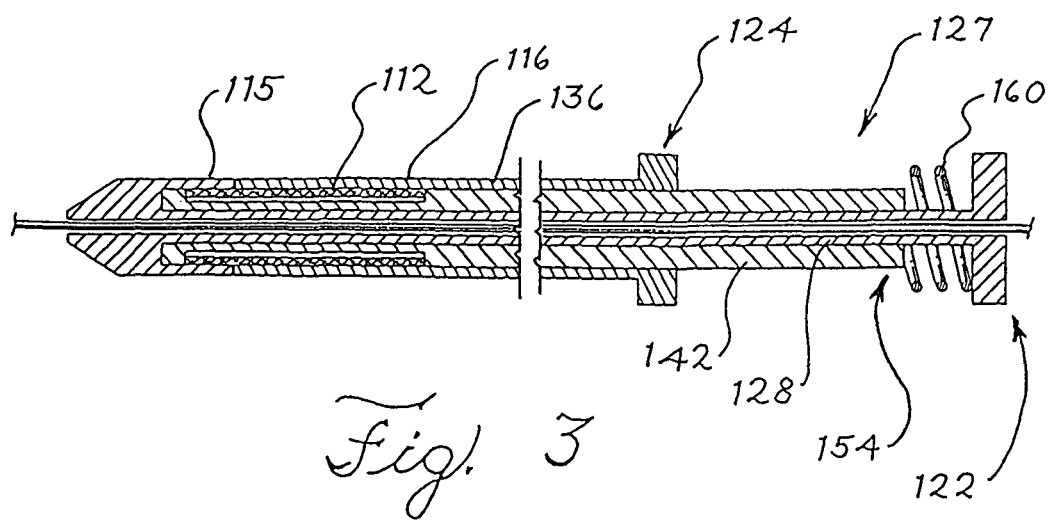
FIGS. 3-5 are cross-sectional views of alternate devices according to various aspects of the invention.

Throughout the specification, the terms "distal" and "distally" shall denote a position, direction, or orientation that is, or a portion of a device that, in use, is positioned generally towards the patient. Accordingly, the terms "proximal" and "proximally" shall denote a position, direction, or orientation that is, or a portion of a device that, in use, is positioned generally away from the patient.

FIG. 1 shows a prosthesis delivery and deployment device 1. The device 1 is adapted to deliver and deploy an expandable prosthesis into a body lumen (not shown) during a medical procedure and may be adapted for use to repair any damaged or diseased body lumen, including but not limited to the esophagus, the bile duct, or a blood vessel. The device 1 comprises a deployment section 2 and a user interface 3. The deployment section 2 travels through the body lumen during the procedure and delivers the prosthesis to a diseased or damaged portion thereof. The user interface 3 remains outside of the body during the procedure and may be manipulated by the operator to position and release or deploy the prosthesis into the body lumen.

The deployment section 2 comprises a prosthesis retention section 10 that is adapted to radially and axially retain proximal and distal ends of a radially expandable prosthesis 12. The prosthesis retention section 10 comprises a cover 14 that covers at least a proximal portion and a distal portion of the prosthesis 12, as shown in FIGS. 1 and 2. The prosthesis 12 comprises a reduced-diameter configuration and an expanded-diameter configuration. The cover 14 retains the proximal and distal portions of the prosthesis 12 in a reduced-diameter configuration for delivery into the body lumen. According to an aspect of the invention, the radially expandable prosthesis 12 may be self-expanding. As such, the cover 14 radially compresses the proximal and distal portions of the prosthesis 12 in a reduced-diameter configuration.

The cover 14 comprises a distal sheath portion 15 that covers a distal portion of the prosthesis 12 and a proximal sheath portion 16 that covers a proximal portion of the prosthesis. The cover 14 is slidably disposed over the prosthesis 12 in a proximal and a distal direction. In particular, the distal sheath 15 may slide distally over the distal portion of the prosthesis 12 and the proximal sheath 16 may slide proximally over the proximal portion of the prosthesis 12. During a procedure, the cover 14 may be withdrawn to expose the self-expanding prosthesis 12, thereby allowing the prosthesis to expand into the body lumen. The prosthesis 12 expands medially into the body lumen; that is, a central portion of the prosthesis 12 expands before the end portions expand.

The prosthesis retention section 10 may further comprise a distal pusher 50 and a proximal pusher 52, as shown in FIG. 2. The distal end of the prosthesis 12 is disposed adjacent a proximal end of the distal pusher 50 and the proximal end of the prosthesis 12 is disposed adjacent a distal end of the proximal pusher 52. The distal and proximal pushers 50, 52 axially restrain the movement of the distal and proximal ends of the prosthesis 12. In particular, the distal pusher 50 prevents the distal end of the prosthesis 12 from moving distally during deployment. Likewise, the proximal pusher 52 prevents the proximal end of the prosthesis 12 from moving proximally during deployment. In this way, the distal and proximal pushers 50, 52 prevent the prosthesis 12 from exhibiting significant axial elongation during deployment.

According to an aspect of the invention, the delivery and deployment device may comprise a distal prosthesis release mechanism 22, a proximal prosthesis release mechanism 24, and an actuation mechanism 27, as shown in FIGS. 1 and 2. The distal and proximal prosthesis release mechanisms 22, 24 may be configured to allow the operator to selectively release the distal and proximal portions of the prosthesis 12 from the delivery and deployment device, respectively. The actuation mechanism 27 may be configured to allow the operator to deploy the proximal release mechanism 24 and the distal release mechanism 22 in a single coordinated movement.

Axially flexible stents have a general tendency to buckle, and therefore have the tendency to deploy unevenly or non-uniformly. Release mechanisms 22, 24 provide distal and proximal fixation during deployment, allowing the prosthesis to expand medially, and generally preventing the prosthesis from axially elongating. By providing distal, as well as proximal fixation during deployment, buckling is suppressed and the stent can deploy more uniformly.

As shown in FIG. 2, the delivery and deployment device may comprise a plurality of elongate members 28, 36, 42 that may be generally tubular. Elongate member 28 extends longitudinally from the distal end of the device to the user interface 3. Distal sheath 15 is disposed on the distal end of the elongate member 28. Distal sheath 15 may be formed separately from elongate member 28 and thereafter fixedly attached thereto. Alternatively, distal sheath 15 may be formed unitarily with elongate member 28 as shown in FIGS. 1 and 2. The distal sheath 15 retains a distal portion of prosthesis 12 in a radially constrained configuration. Elongate member 28 may further comprise an inner lumen 32 that extends longitudinally therethrough. Inner lumen 32 is configured to receive a guide wire 34 (shown in FIG. 1).

Elongate member 36 comprises an inner lumen 40 extending longitudinally therethrough and is disposed radially about elongate member 28. Proximal sheath 16 comprises the distal end of elongate member 36. Proximal sheath 16 may be formed separately from elongate member 36 and thereafter fixedly attached thereto. Alternatively, proximal sheath 16 may be formed unitarily with elongate member 36 as shown in FIGS. 1 and 2. Elongate member 36 extends proximally from the distal end of the proximal sheath to the user interface 3. The proximal end of elongate member 36 is disposed distally with respect to the proximal end of elongate member 28.

Elongate member 42 comprises a distal end, a proximal end, and an inner lumen 44 extending longitudinally therethrough. Elongate member 42 extends proximally from the prosthesis retention section 10 to the user interface 3. The proximal end of elongate member 42 is disposed between the proximal end of elongate member 36 and the proximal end of elongate member 28. Elongate member 42 is slidably disposed within lumen 40 of the elongate member 36. Elongate member 28 is slidably disposed within lumen 44 of elongate member 42 and lumen 40 of elongate member 36. Elongate members 28, 42 form the distal release mechanism 22 and elongate members 36, 42 form the proximal release mechanism 24. Distal and proximal release mechanisms 22, 24 are adapted to release the distal and proximal portions of the prosthesis 12 into the body lumen.

Hereinafter, for the sake of simplicity, elongate members 28, 36, 42 shall be referred to as inner elongate member 28, outer elongate member 36, and middle elongate member 42. As shown in FIG. 2, a prosthesis 12 may be disposed on middle elongate member 42 between distal and proximal pushers 50, 52. The distal pusher 50 has a proximal-facing surface 51 that faces axially towards the distal end of the prosthesis 12. The proximal pusher 52 has a distal-facing surface 53 that faces axially towards the proximal end of the prosthesis 12. Distal and proximal pushers 50, 52 have a fixed relation to one another. During deployment, the distal sheath 15 is withdrawn distally over the distal end of the prosthesis 12 and the distal pusher 50 pushes the distal end of the prosthesis 12 in a proximal direction. Likewise, the proximal sheath 16 is withdrawn proximally over the proximal end of the prosthesis 12 and the proximal pusher 52 pushes the proximal end of the prosthesis 12 in a distal direction.

The actuation mechanism 27, as shown in FIGS. 1 and 2, allows the operator to deploy the prosthesis in a single coordinated movement. Actuation mechanism 27 comprises a first handle portion 30 and a second handle portion 38. First handle portion 30 is coupled to the distal sheath 15 and may be disposed on the proximal end of inner elongate member 28. The second handle portion 38 is coupled to the proximal sheath 16 and may be disposed on the proximal end of outer elongate member 36. To deploy the actuation mechanism 27, the second handle portion 38 is slid proximally towards the first handle portion 30 and/or the first handle portion 30 is slid distally towards the second handle portion 38. This action causes the proximal sheath 16 to retract from the proximal portion of the prosthesis 12 and the distal sheath 15 to retract from the distal portion of the prosthesis 12.

The operator may wish to control the deployment of the prosthesis 12. For example, the operator may wish to withdraw the proximal sheath 16 prior to the distal sheath 15, the distal sheath 15 prior to the proximal sheath 16, or the distal and proximal sheaths 15, 16 generally concurrently. Alternatively, or additionally, the operator may wish to deploy the prosthesis 12 so that the distal end is released before the proximal end, the proximal end is released before the distal end, or the proximal and distal ends are released generally concurrently.

The distal release mechanism 22 has a resistance D that is the force that is required to retract the distal sheath 15. Resistance D is generally a function of many factors, including friction between elongate members 28, 42 and friction between distal sheath 15 and the prosthesis 12. Similarly, the proximal release mechanism 24 has a resistance P that is the force that is required to retract the proximal sheath 16. Resistance P is generally a function of many factors, including friction between elongate members 36, 42 and friction between proximal sheath 16 and the prosthesis 12. When the operator deploys the actuation mechanism 27, the manner of deployment will be a function of resistance D and resistance P. For example, when resistance D is greater than resistance P, the proximal sheath 16 will retract and the distal sheath 15 will remain stationary. Conversely, when resistance P is greater than resistance D, the distal sheath 15 will retract and the proximal sheath 16 will remain stationary.

According to an aspect of the present invention, the delivery and deployment device 1 may comprise a biasing compensator 60. Biasing compensator 60 regulates the relationship between resistance P and resistance D, thereby giving the operator control over the manner of deployment of the proximal sheath 16 and the distal sheath 15. At least one or both of the proximal release mechanism 24 and the distal release mechanism 22 may comprise a biasing compensator 60.

Various devices and means are contemplated for regulating resistances D and P. For example, resistances D and P may be regulated by controlling friction in the distal release mechanism 22 or the proximal release mechanism 24. In one embodiment, the middle elongate member 42 and/or the outer elongate member 36 may comprise a material that is selected to influence the friction between middle elongate member 42 and the outer elongate member 36. For example, a lubricious biocompatible coating or surface treatment may be applied to one or both of the middle and outer elongate members 36, 42. Examples of suitable coatings include biocompatible coatings comprising silicone or polytetrafluoroethylene ("PTFE"). By applying a lubricious coating as described, the resistance P will decrease in relation to resistance D, thereby regulating the manner of deployment. It should be apparent that a similar effect will be achieved by applying a friction-increasing coating or surface treatment to one or both of the inner and middle elongate members 28, 36.

Other devices and means for controlling the friction in the distal and proximal release mechanisms 22, 24 are contemplated. For example, at least one of the distal and proximal release mechanisms 22, 24 may comprise an interference member that is adapted to selectively influence the friction in the distal and/or proximal release mechanism 22, 24. Interference member may be a gasket or o-ring that is compressed within an annular space between the inner elongate member 28 and the middle elongate member 36, or within an annular space between the outer elongate member 36 and the middle elongate member 42. The gasket may be selectively inflatable and deflatable to effect the relationship between resistance P and resistance D. Each of the distal and proximal release mechanisms 22, 24 may comprise an interference member as described.

The delivery and deployment device may further comprise a limiting member 54 for limiting the displacement of the proximal sheath 16 and the distal sheath 15 during deployment. Limiting member 54 may comprise a stop 55 disposed between the proximal handle 30 and the distal handle 38. As shown in FIG. 2, stop 55 may be disposed on the proximal end of elongate member 42. Stop 55 comprises a proximal limit 56 and a distal limit 58. Proximal limit 56 is adapted to limit the proximal displacement of the proximal sheath 16. Distal limit 58 is adapted to limit the distal displacement of the distal sheath 15.

FIG. 3 illustrates a delivery and deployment device according to another aspect of the present invention. The device comprises a prosthesis 112 disposed on a distal portion thereof. A distal sheath 115 removably covers a distal portion of the prosthesis 112 and a proximal sheath 116 removably covers a proximal portion of the prosthesis 112. The delivery and deployment device comprises a distal prosthesis release mechanism 122, a proximal prosthesis release mechanism 124, and an actuation mechanism 127 for actuating the distal release mechanism 122 and the proximal release mechanism 124 in a single coordinated movement. The delivery and deployment device further comprises a limiting member 154. Distal release mechanism 122 has a resistance D and proximal release mechanism 124 has a resistance P.

The distal release mechanism 122 comprises a biasing compensator 160. Biasing compensator 160 biases resistance D with respect to resistance P. Biasing compensator 160 regulates the displacement of the distal sheath 115 and the proximal sheath 116 during deployment. As shown in FIG. 3, biasing compensator 160 may comprise at least one spring disposed between inner elongate member 128 and middle elongate member 142. Biasing compensator 160 may comprise a compression spring, selected so that resistance D is greater than or equal to resistance P. Alternatively, biasing compensator 160 may comprise a tension spring, selected so that resistance D is less than or equal to resistance P.

By selecting an appropriate biasing compensator 160, the operator can control the manner of deployment. For example, the biasing compensator 160 may be selected so that the distal sheath 115 moves prior to the proximal sheath 116, so that the proximal sheath 116 moves prior to the distal sheath 115, or so that the distal and proximal sheaths 115, 116 move generally concurrently. Furthermore, the biasing compensator 160 may be selected so that the distal end of the prosthesis 112 is released prior to the proximal end of the prosthesis 112, so that the proximal end of the prosthesis 112 is released prior to the distal end of the prosthesis 112, or so that the proximal and distal ends of the prosthesis are released generally concurrently.

Figure 4:
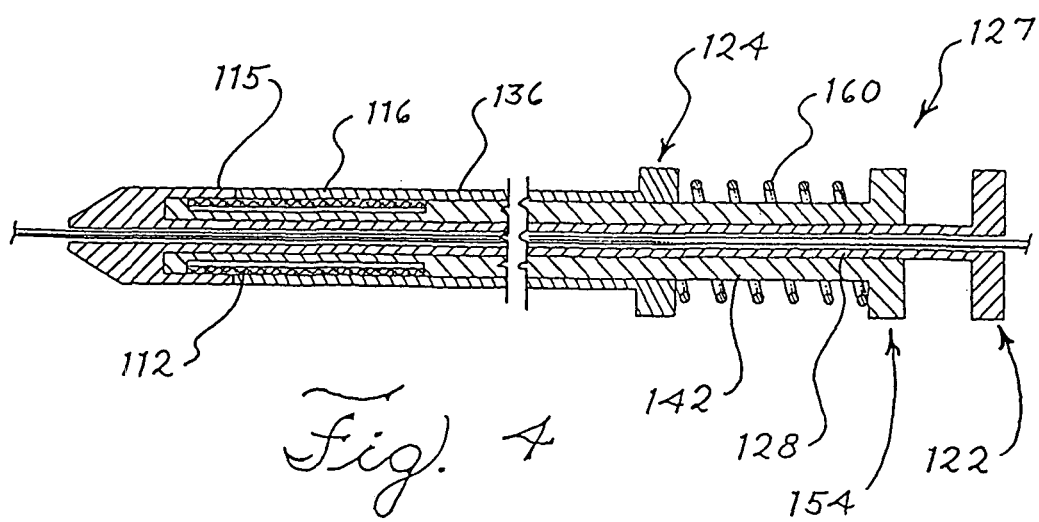

FIG. 4 shows another delivery and deployment device according to an aspect of the invention. The device of FIG. 4 is similar to the device of FIG. 3 except that the proximal release mechanism 124 comprises a biasing compensator 160. The biasing compensator 160 comprises at least one spring disposed between outer elongate member 136 and middle elongate member 142. The spring biases the resistance P of proximal release mechanism 124, thereby regulating the displacement of the distal sheath 115 and the proximal sheath 116 during deployment.

Figure 5:
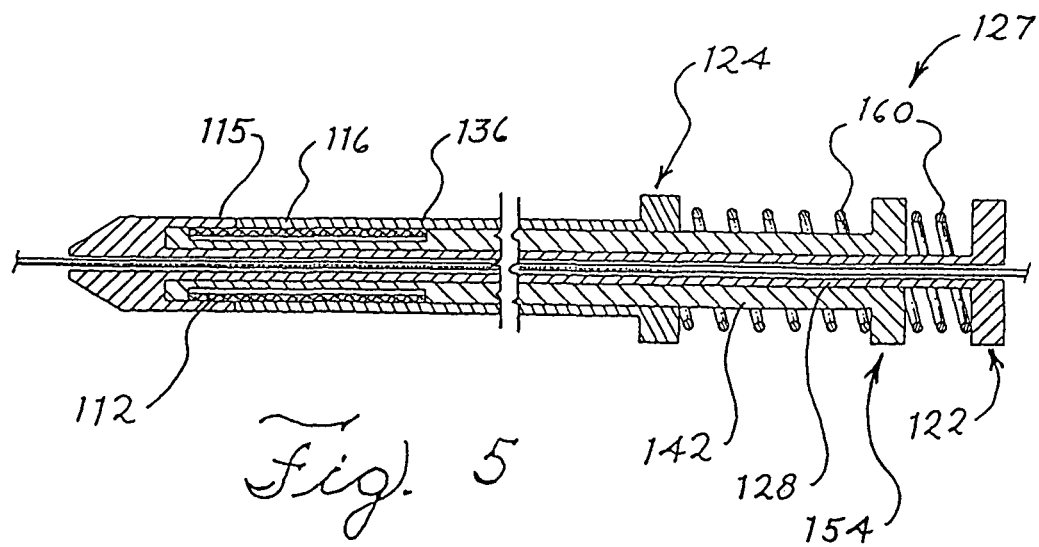

FIG. 5 shows yet another device according to an aspect of the invention in which biasing compensator 160 comprises a plurality of springs. One or more springs are disposed between the inner and middle elongate members 128, 142 and one or more springs are disposed between the outer and middle elongate members 136, 142. Biasing compensator 160 may be chosen so that resistances D, P are generally dissimilar, or so that resistances D, P are generally similar. Each of the springs may comprise a compression spring, or each may comprise a tension spring. Alternatively, the springs may comprise both tension springs and compression springs.

In a further aspect, at least one of the distal release mechanism 122 and the proximal release mechanism 124 may comprise a plurality of biasing elements. For example, the proximal release mechanism 124 of FIG. 4 may include a plurality of springs arranged in series. At least one of the springs may be a compression spring and at least one of the springs may be a tension spring. The tension spring may be selected so that the resistance P is initially less than resistance D. The compression spring causes resistance P to increase during deployment.

In one embodiment, a biasing compensator 160 may be provided and comprise a plurality of biasing elements, such as springs. Each of the distal and proximal release mechanisms 122, 124 may include at least one of the plurality of biasing elements. For example, the proximal release mechanism 124 may comprise a tension spring and a compression spring, and the distal release mechanism 122 may comprise a compression spring. The springs may be selected so that when the actuation mechanism 127 is deployed, the proximal sheath 116 moves prior to the distal sheath 115 but halts before the proximal end of the prosthesis 112 is released. Accordingly, the distal sheath 115 can retract over the prosthesis 112 and release the distal end of the prosthesis prior to releasing the proximal end of the prosthesis.

Figure 7:
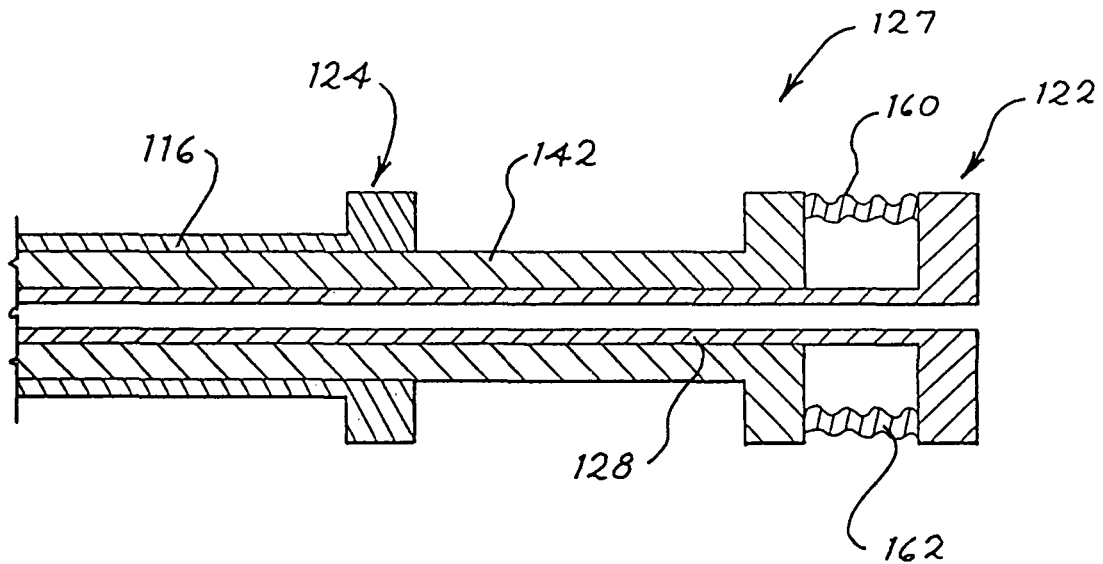
FIGS. 7-8 are cross-sectional views of proximal portions of delivery and deployment devices including various biasing compensators.
Figure 8:
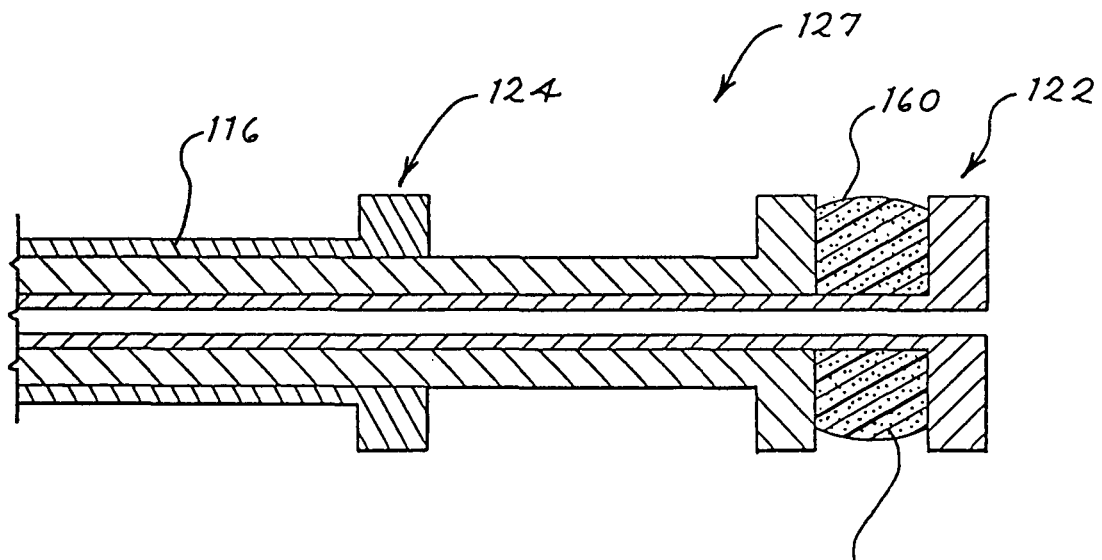

FIGS. 7 and 8 illustrate delivery and deployment devices having biasing compensators 160 with alternative biasing elements. In FIG. 7, the biasing compensator 160 comprises a generally flexible tubular member 162 disposed between the inner elongate member 128 and middle elongate member 142. The tubular member 162 comprises a lumen that defines an inner diameter that is generally greater than the outer diameter of the inner elongate member 128. The tubular member 162 is longitudinally compressible and may be configured as a bellows that is vented to permit the tubular structure to collapse. Tubular member 162 is configured to have a desired longitudinal stiffness so that it biases resistance D with respect to resistance P. Tubular member 162 may exhibit purely elastic, purely plastic, or a combination of elastic and plastic properties when longitudinally compressed. Tubular member 162 may comprise various materials, such as natural or synthetic rubber, or a thermoplastic elastomer.

The biasing compensator 160 may alternatively include a compressible gasket 164, such as the foam gasket shown in FIG. 8. The gasket 164 is longitudinally compressible and may comprise non-recoverable, partially-recoverable, or fully-recoverable foam materials. Suitable materials include, but are not limited to, polyurethane and polyolefin elastomers. In general, the selection of an appropriate biasing member or members to regulate resistance D, P and thereby regulate the deployment of distal and proximal release mechanisms 122, 124 will be readily understood by one of ordinary skill in the art.

Figure 6:
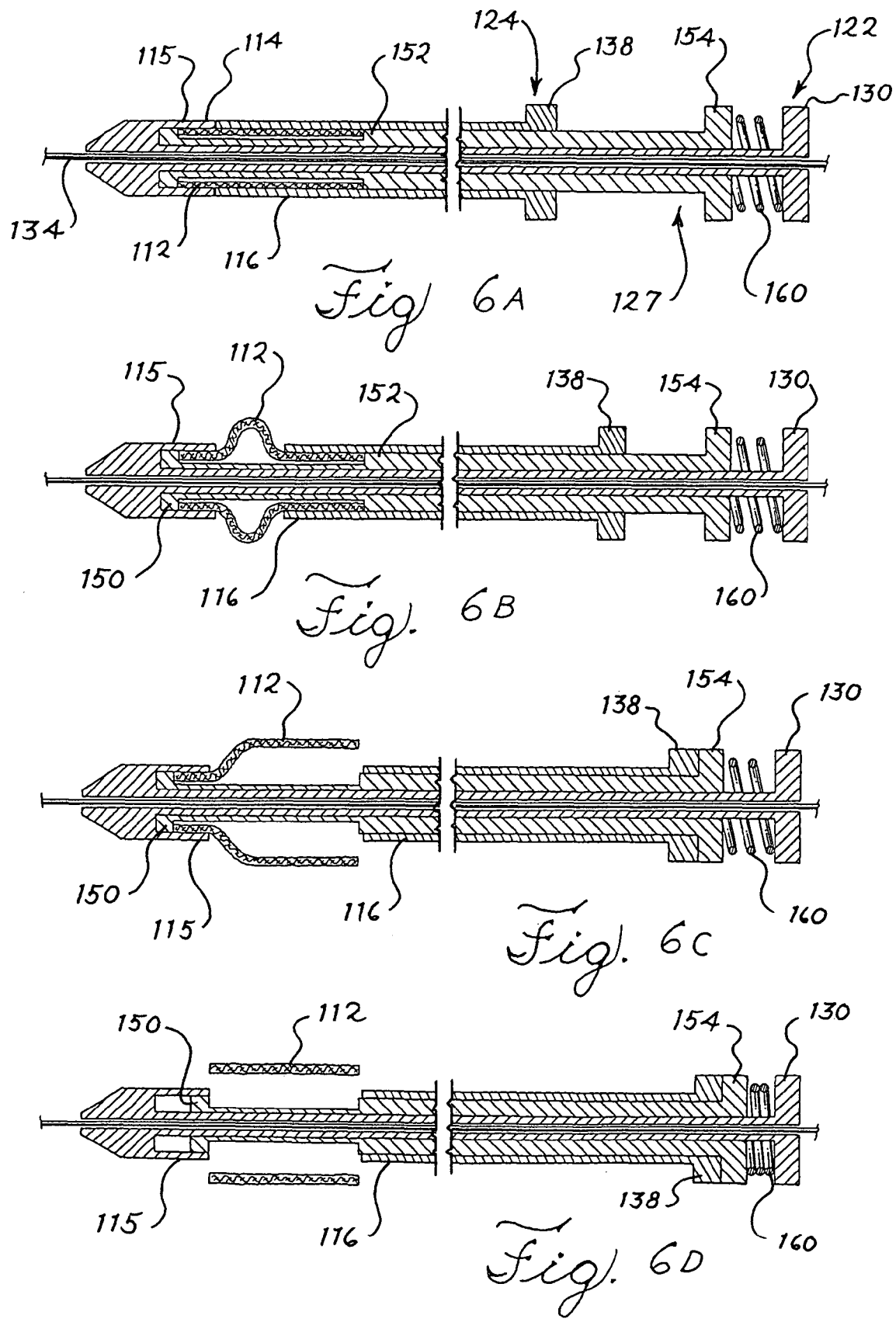
FIGS. 6A-6D are cross-sectional views of an exemplary delivery and deployment device in various stages of deployment.

A method of delivering and deploying a prosthesis into a body lumen according to an aspect of the present invention will now be described with reference to FIGS. 6A through 6D. First, access is provided to the body lumen. For example, if the prosthesis is used to repair an artery, an incision may be made and access provided through an artery, such as the femoral or brachial arteries. Next, a guide wire 134 is introduced into the body lumen and advanced until the tip of the guide wire is beyond the region into which the prosthesis 112 is to be deployed. The delivery and deployment device is then inserted through the body lumen over the guide wire 134 and positioned by radiographic techniques that are generally known in the art. At this stage, the prosthesis 112 is fully retained in the delivery and deployment device in a radially-constrained configuration by the cover 114 as shown in FIG. 6A. The distal sheath 115 covers the distal portion of the prosthesis 112 and the proximal sheath 116 covers the proximal portion of the prosthesis 112.

Once the prosthesis 112 is properly positioned, the delivery and deployment device is ready for deployment. To deploy the prosthesis, the operator actuates the actuation mechanism 127. The operator secures the first handle portion 130 and the second handle portion 138. The operator slides the first handle portion 130 distally and the second handle portion 138 proximally so that the handle portions 130, 138 slide towards one another, as shown in FIGS. 6B-6D.

FIGS. 6B-6D show the deployment of the prosthesis 112 in successive stages. Although the deployment is described in terms of stages, it should be understood that in practice, the deployment may occur in a single coordinated movement. In this example, biasing compensator 160 is selected so that resistance D is initially greater than resistance P, however biasing compensator 160 may be selected so that resistance D is initially less than resistance P or so that resistances D, P are generally similar. During the initial stage of deployment, biasing compensator 160 causes the proximal sheath 116 to retract proximally over the prosthesis 112 and the middle elongate member 142 while the distal sheath 115 remains stationary. As the proximal sheath 116 moves proximally over the prosthesis 112, the proximal pusher 152 pushes the prosthesis 112 distally, preventing the proximal end of the prosthesis from sliding proximally. A medial portion of the prosthesis 112 is exposed and expands radially outwardly as shown in FIG. 6B. At this point, distal and proximal prosthesis ends are radially and axially retained by the distal and proximal release mechanisms 122, 124 respectively. Because the ends of the prosthesis 112 are axially retained, the prosthesis is prevented from exhibiting significant axial shortening or lengthening.

At this point, the prosthesis 112 is not yet anchored in the body lumen. Therefore, if necessary, the prosthesis 112 may be rotated or repositioned. Further, if it is necessary to abort the procedure and remove the prosthesis 112, the prosthesis 112 may be recaptured. This is done simply by sliding the first handle portion 130 proximally away from the second handle portion 138, and the second handle portion 138 distally away from the first handle portion 130, thereby causing distal sheath 115 and proximal sheath 116 to move towards one another. The distal and proximal sheaths 115, 116 compress the expanded medial portion back into a constrained configuration.

In FIG. 6C, the proximal sheath 116 is withdrawn from the prosthesis 112 so that the proximal end of the prosthesis 112 has been released and the proximal portion of the prosthesis 112 has expanded into the body lumen (not shown). The proximal sheath 116 will continue to retract over middle elongate member 142 so long as resistance D is greater than resistance P. However, the proximal sheath is prevented from retracting beyond limiting member 154. Limiting member 154 causes resistance P to increase until resistance P is greater than resistance D. Thereafter, the proximal sheath 116 will become stationary and the distal sheath 115 can move. The distal sheath 115 retracts distally relative to the distal end of prosthesis 112 and the distal pusher 150. As the distal sheath 115 retracts over the prosthesis 112, the distal pusher 150 pushes the distal end of prosthesis 112 proximally, causing the distal portion of the prosthesis to expand into the body lumen.

FIG. 6D shows the delivery and deployment device in a fully deployed state wherein both the distal and proximal ends of the prosthesis 112 have been released into the body lumen. Once the prosthesis 112 has been released into the body lumen, the delivery and deployment device and the guide wire may be removed from the body lumen.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A device for delivering and deploying a radially expandable prosthesis, the device comprising:
   a proximal release mechanism comprising a proximal sheath radially disposed over a proximal portion of a prosthesis, wherein the proximal sheath is slidable proximally relative to the prosthesis to release the proximal portion of the prosthesis, the proximal release mechanism comprising a first resistance;
   a distal release mechanism comprising a distal sheath radially disposed over a distal portion of the prosthesis, wherein the distal sheath is slidable distally relative to the prosthesis to release the distal portion of the prosthesis, the distal release mechanism comprising a second resistance;
   an actuation mechanism for actuating the proximal and distal release mechanisms in a single coordinated movement; and
   a biasing compensator having a longitudinally-directed biasing force acting directly on at least one of the proximal sheath and the distal sheath, whereby the biasing compensator requlates the relationship between the first resistance and the second resistance.

2. The device according to claim 1 wherein at least one of the proximal and distal release mechanisms comprises the biasing compensator.

3. The device according to claim 1 wherein the biasing compensator comprises a spring.

4. The device according to claim 3 wherein the biasing compensator comprises a compression spring.

5. The device according to claim 3 wherein the biasing compensator comprises a tension spring.

6. The device according to claim 1 wherein the biasing compensator comprises a bellows.

7. The device according to claim 1 wherein the biasing compensator comprises a compressible gasket.

8. The device according to claim 1 wherein the device comprises a plurality of biasing elements, each of the distal and proximal release mechanisms including at least one of the plurality of biasing elements.

9. The device according to claim 1 further comprising a limiting member for limiting the displacement of at least one of the proximal sheath and the distal sheath.

10. The device according to claim 1 wherein the biasing compensator increases at least one of the first resistance and the second resistance.

11. The device according to claim 10 wherein the biasing compensator decreases the other of the second resistance and the first resistance.

12. The device according to claim 1 wherein the biasing compensator decreases at least one of the first resistance and the second resistance.

13. The device according to claim 1 wherein the biasing compensator comprises at least one compression spring and at least one tension spring.

14. The device according to claim 13, wherein the at least one compression spring is in series with the at least one tension spring.

15. A device for delivering and deploying a radially expandable prosthesis, the device comprising:
    a first elongate member comprising a lumen and having a radially expandable prosthesis disposed over a distal portion of the first elongate member;
    a second elongate member slidably disposed within the lumen of the first elongate member and comprising a distal sheath for releasably retaining a distal portion of the prosthesis, wherein the delivery and deployment device has a distal release resistance;
    a third elongate member comprising a lumen, the third elongate member slidably disposed over the first elongate member and comprising a proximal sheath for releasably retaining a proximal portion of the prosthesis, wherein the delivery and deployment device has a proximal release resistance;
    an actuation mechanism for moving the second elongate member distally relative to the first elongate member and the third elongate member proximally relative to the first elongate member to release the distal and the proximal portions of the prosthesis in a single coordinated movement; and
    a biasing compensator disposed between the proximal end of the second elongate member and the proximal end of the third elongate member, the biasing compensator having a longitudinally-directed biasing force for regulating the relationship between the distal release resistance and the proximal release resistance.

16. The device according to claim 15 wherein the biasing compensator is selected from the group consisting of a spring, a bellows, and a compressible gasket.

17. The device according to claim 15 wherein the biasing compensator is directly connected to at least one of the second elongate member and the third elongate member.

18. The device according to claim 15 wherein the delivery and deployment device comprises a plurality of biasing elements, one or more biasing element being connected to each of the second and third elongate members, the biasing elements selected from the group consisting of a spring, a bellows, and a compressible gasket.

19. The device according to claim 15 further comprising a limiting member for limiting the displacement of at least one of the proximal sheath and the distal sheath.

20. A device for delivering and deploying a radially expandable prosthesis, the device comprising:
    a proximal release mechanism comprising a proximal sheath radially disposed over a proximal portion of a prosthesis, wherein the proximal sheath is slidable proximally relative to the prosthesis to release the proximal portion of the prosthesis, the proximal release mechanism comprising a first resistance;
    a distal release mechanism comprising a distal sheath radially disposed over a distal portion of the prosthesis, wherein the distal sheath is slidable distally relative to the prosthesis to release the distal portion of the prosthesis, the distal release mechanism comprising a second resistance;
    an actuation mechanism for actuating the proximal and distal release mechanisms in a single coordinated movement; and
    a longitudinally compressible biasing compensator acting directly on at least one of the proximal sheath and the distal sheath, whereby the biasing compensator regulates the relationship between the first resistance and the second resistance.

21. A device for delivering and deploying a radially expandable prosthesis, the device comprising:
    a delivery catheter having a proximal end and a distal end;
    a radially expandable prosthesis disposed over a distal end portion of the delivery catheter;
    a proximal release mechanism comprising a proximal sheath disposed over and releasably retaining a proximal portion of the prosthesis, the proximal release mechanism comprising a first resistance;

a distal release mechanism comprising a distal sheath disposed over and releasably retaining a distal end portion of the prosthesis, the distal release mechanism comprising a second resistance;

an actuation mechanism disposed at a proximal end portion of the delivery catheter and comprising a first handle portion coupled to the proximal release mechanism and a second handle portion coupled to the distal release mechanism, wherein sliding the first handle portion with respect to the second handle portion actuates the proximal and distal release mechanisms at the same time;

the actuation mechanism further comprising a biasing compensator having a longitudinally-directed biasing force acting on at least one of the proximal sheath and the distal sheath, whereby the biasing compensator regulates the relationship between the first resistance and the second resistance.

\* \* \* \* \*